(12) United States Patent
Lee et al.

(10) Patent No.: US 9,597,516 B2
(45) Date of Patent: Mar. 21, 2017

(54) WIRELESS COMMUNICATION DEVICE FOR MEDICAL TELEMETRY

(75) Inventors: David W. Lee, Apple Valley, MN (US); William C. Phillips, Brooklyn Park, MN (US); Yu Wang, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 796 days.

(21) Appl. No.: 13/360,496

(22) Filed: Jan. 27, 2012

(65) Prior Publication Data

US 2013/0194106 A1    Aug. 1, 2013

(51) Int. Cl.
*G08C 17/02*    (2006.01)
*A61N 1/372*    (2006.01)

(52) U.S. Cl.
CPC ..... *A61N 1/37223* (2013.01); *A61N 1/37252* (2013.01)

(58) Field of Classification Search
CPC .................. A61N 1/37223; A61N 1/37252
USPC ......... 340/870.3; 307/64; 375/219; 600/437; 607/60; 700/21
See application file for complete search history.

(56) References Cited

U.S. PATENT DOCUMENTS

| | | | |
|---|---|---|---|
| 5,683,432 A | 11/1997 | Goedeke et al. | |
| 6,211,830 B1* | 4/2001 | Monma et al. | 343/702 |
| 7,720,544 B2 | 5/2010 | Christman et al. | |
| 7,813,709 B2 | 10/2010 | Yamamoto et al. | |
| 2003/0114897 A1 | 6/2003 | Von Arx et al. | |
| 2006/0103584 A1* | 5/2006 | Su et al. | 343/860 |
| 2006/0252391 A1* | 11/2006 | Poilasne | H01Q 19/00 455/121 |
| 2009/0248112 A1 | 10/2009 | Mumbru et al. | |
| 2010/0036508 A1* | 2/2010 | Ramakrishnan et al. | 700/21 |
| 2010/0100157 A1* | 4/2010 | Nghiem et al. | 607/60 |
| 2010/0179618 A1* | 7/2010 | Marnfeldt et al. | 607/60 |
| 2010/0331682 A1* | 12/2010 | Stein et al. | 600/437 |
| 2011/0193761 A1* | 8/2011 | Shinkai | H01Q 1/38 343/817 |
| 2011/0316750 A1* | 12/2011 | Yen | 343/702 |

FOREIGN PATENT DOCUMENTS

WO    2006939364 A1    9/2006

OTHER PUBLICATIONS

International Search Report and Written Opinion of international application No. PCT/US2013/020237, dated Jul. 11, 2013, 9 pp.

* cited by examiner

*Primary Examiner* — Sisay Yacob
(74) *Attorney, Agent, or Firm* — Shumaker & Sieffert, P.A.

(57) ABSTRACT

A device includes an antenna, a parasitic element, and a telemetry control module. The parasitic element modifies a radiation pattern of the antenna. The parasitic element has an impedance value that is adjustable, and the radiation pattern of the antenna depends on the impedance value of the parasitic element. The telemetry control module is configured to transmit data to a medical device using the antenna, receive data from the medical device using the antenna, and detect communication errors using data that is received from the medical device. Additionally, the telemetry control module is configured to adjust the impedance value of the parasitic element in response to detection of communication errors.

32 Claims, 6 Drawing Sheets

WIRELESS COMMUNICATION DEVICE FOR MEDICAL TELEMETRY

TECHNICAL FIELD

The disclosure relates to wireless communication devices, and more particularly, to wireless communication devices for medical telemetry.

BACKGROUND

A variety of different types of medical devices may include wireless telemetry functionality. A clinician or a patient may use a programming device to wirelessly communicate with such medical devices. For example, a clinician or patient may use a programming device to wirelessly retrieve data from a medical device and to wirelessly program the medical device. Medical devices including wireless telemetry functionality may include, but are not limited to, cardiac electrical therapy devices, neurostimulation devices, and drug pump devices. Example cardiac electrical therapy devices may include pacemakers, cardioverters, and/or defibrillators. Neurostimulation devices may be used to stimulate targets that include, but are not limited to, spinal cord targets, deep brain stimulation (DBS) targets, gastric nerves, pelvic nerves, peripheral nerves, and/or a variety of organs such as the heart, stomach, bladder, or the like. Example drug pump devices may be configured to deliver medication for treatment of chronic pain or diabetes. Medical devices that include wireless telemetry functionality may be implanted in a patient or may be attached externally to the patient in some examples.

A programming device may include a variety of different functionalities and may have a variety of different form factors, depending on the application for which the programming device is tailored. In some examples, a programming device may be tailored to a clinician that may use the programming device in order to program a medical device or retrieve information from the medical devices. In other examples, a programming device may be tailored for more limited use by a patient so that the patient may program and monitor operation of their medical device.

SUMMARY

A telemetry device of the present disclosure may be configured to wirelessly communicate with a variety of different types of medical devices. The telemetry device may include a radio-frequency (RF) telemetry antenna that the telemetry device may use to transmit and receive data. Additionally, the telemetry device includes a parasitic element that modifies the radiation pattern of the RF telemetry antenna. The parasitic element may have an adjustable impedance value that may be controlled by a telemetry control module of the telemetry device. The radiation pattern of the RF telemetry antenna may depend on the impedance value of the parasitic element, as set by the telemetry control module.

During operation of the telemetry device, the telemetry control module may selectively adjust the impedance value of the parasitic element in order to control the radiation pattern and receive pattern of the RF telemetry antenna (e.g., the directional strength of the radio waves transmitted from the RF telemetry antenna). The telemetry control module may adjust the impedance value of the parasitic element in response to the detection of communication errors that occur during communication between the telemetry device and a medical device with which the telemetry device is communicating. The telemetry control module may adjust the impedance value of the parasitic element in response to the detection of communication errors since the detection of errors during communication may indicate that communication between the telemetry device and the medical device is not reliable using the current radiation pattern. The adjustment of the impedance value of the parasitic element may change the radiation pattern of the RF telemetry antenna, and may therefore lead to a more reliable communication link between the telemetry device and the medical device. The telemetry device of the present disclosure may have a handheld mobile form factor that allows a user to hold and operate the telemetry device using a single hand.

In some examples according to the present disclosure, a device comprises an antenna, a parasitic element, and a telemetry control module. The parasitic element modifies a radiation pattern of the antenna. The parasitic element has an impedance value that is adjustable, and the radiation pattern of the antenna depends on the impedance value of the parasitic element. The telemetry control module is configured to transmit data to a medical device using the antenna, receive data from the medical device using the antenna, and detect communication errors using data that is received from the medical device. Additionally, the telemetry control module is configured to adjust the impedance value of the parasitic element in response to detection of communication errors.

In some examples according to the present disclosure, a system comprises a medical device and a telemetry device configured to wirelessly communicate with the medical device. The telemetry device comprises an antenna, a parasitic element, and a telemetry control module. The parasitic element modifies a radiation pattern of the antenna. The parasitic element has an impedance value that is adjustable, and the radiation pattern of the antenna depends on the impedance value of the parasitic element. The telemetry control module is configured to transmit data to the medical device using the antenna, receive data from the medical device using the antenna, and detect errors in at least one of the data received from the medical device and the data transmitted to the medical device. Additionally, the telemetry control module is configured to adjust the impedance value of the parasitic element in response to detection of errors in at least one of the data received from the medical device and the data transmitted to the medical device.

In some examples according to the present disclosure, a method comprises modifying a radiation pattern of an antenna using a parasitic element. The parasitic element has an impedance value that is adjustable, and the radiation pattern of the antenna depends on the impedance value of the parasitic element. Additionally, the method comprises transmitting data to a medical device using the antenna, receiving data from the medical device using the antenna, and detecting communication errors using data that is received from the medical device. The method further comprises adjusting the impedance value of the parasitic element in response to detection of communication errors.

In some examples according to the present disclosure, a system comprises means for modifying a radiation pattern of an antenna using a parasitic element. The parasitic element has an impedance value that is adjustable, and the radiation pattern of the antenna depends on the impedance value of the parasitic element. Additionally, the system comprises means for transmitting data to a medical device using the antenna, means for receiving data from the medical device using the antenna, and means for detecting communication errors using data that is received from the medical device. The system further comprises means for adjusting the impedance value of the parasitic element in response to detection of communication errors.

In some examples according to the present disclosure, a computer-readable storage medium comprises instructions that cause a programmable processor to modify a radiation pattern of an antenna using a parasitic element. The parasitic element has an impedance value that is adjustable, and the radiation pattern of the antenna depends on the impedance value of the parasitic element. The computer-readable storage medium further comprises instructions that cause the programmable processor to transmit data to a medical device using the antenna, receive data from the medical device using the antenna, detect communication errors using data that is received from the medical device, and adjust the impedance value of the parasitic element in response to detection of communication errors.

The details of one or more examples are set forth in the accompanying drawings and the description below. Other features, objects, and advantages will be apparent from the description and drawings, and from the claims.

DETAILED DESCRIPTION

Figure 1:
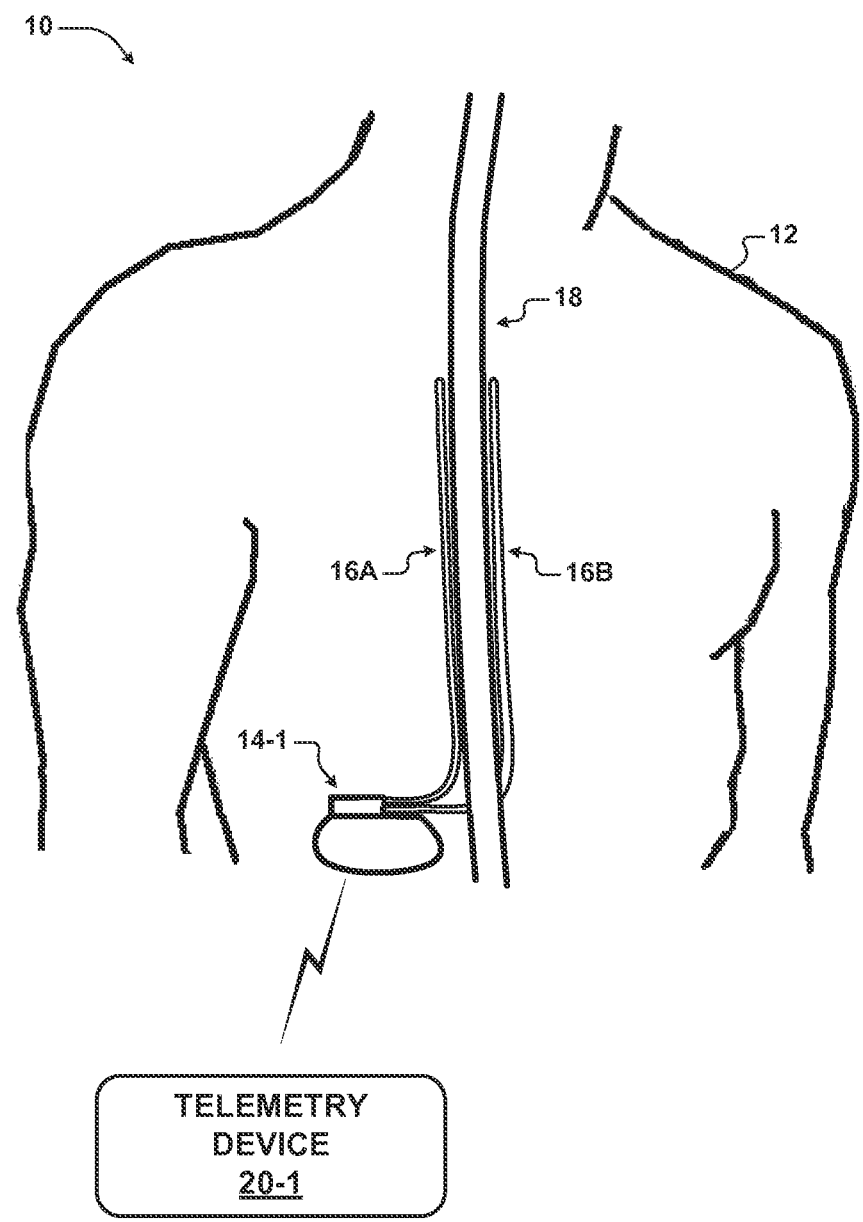
FIG. 1 shows a system that includes an example telemetry device in communication with a spinal cord stimulation device.

A telemetry device of the present disclosure may be configured to wirelessly communicate with a variety of different medical devices. The telemetry device may be used to wirelessly receive signals, e.g., to retrieve data from a medical device and/or wirelessly transmit signals, e.g., to program a medical device. The telemetry device may include a variety of different programming and/or data retrieval functionalities depending on the type of medical device with which the telemetry device is configured to interact. Additionally, the telemetry device may be configured for patient use and/or clinician use, again depending on the intended use of the telemetry device. A variety of different possible configurations and uses are described in more detail with respect to FIGS. 1 and 2. The intended user of the telemetry device, whether patient or clinician, may be referred to herein as a "user" of the telemetry device.

The telemetry device of the present disclosure may include radio-frequency (RF) telemetry functionality. For example, the telemetry device may communicate in the Medical Implant Communication Service (MICS) band and the Medical Data Service (MEDS) band between 401 MHz and 406 MHz. Additionally, the telemetry device may communicate in other frequency bands, including, but not limited to a 2.4 GHz industrial, scientific and medical (ISM) band for Bluetooth and IEEE 802.11 b/g/n standards. In some examples, the telemetry device may use RF telemetry to transfer and receive data at configurable rates of up to approximately 380 kbps, and may communicate with medical devices over a wide range of distances, e.g., up to approximately 10 meters. Because RF telemetry devices may not require close proximity for communication, but instead may communicate over a wide range of distances, RF telemetry may also be referred to as "distance telemetry" in some examples.

The telemetry device may include an RF telemetry antenna (e.g., a helical coil antenna) that the telemetry device may use to transmit and receive data. For example, the telemetry device may use the RF telemetry antenna to transmit/receive data to/from a medical device that includes RF telemetry functionality. The telemetry device includes a telemetry control module that may include electronic hardware, firmware, and/or software that is configured to both transmit data and receive data using the RF telemetry antenna. The telemetry control module may be connected to the RF telemetry antenna with a transmission line (e.g., an antenna feed), and may transmit data to the antenna and receive data from the antenna via the transmission line.

The telemetry device also includes a parasitic element that modifies the radiation pattern and receive pattern of the RF telemetry antenna. In general, the parasitic element may reflect energy that reaches it in order to modify the radiation pattern of the RF telemetry antenna, but may not be electrically connected to the transmission line of the RF antenna. The parasitic element may have an impedance value that is adjustable, and that may be controlled by the telemetry control module of the telemetry device. The radiation pattern of the RF telemetry antenna may depend on the impedance value of the parasitic element. In other words, a change in the impedance value of the parasitic element may change the radiation pattern of the RF telemetry antenna. During operation of the telemetry device, the telemetry control module may selectively adjust the impedance value of the parasitic element in order to control the radiation pattern of the RF telemetry antenna (i.e., the telemetry device).

The parasitic element may include a conductor element and a variable impedance that is connected to the conductor element. In some examples, the conductor element may be a conductive object, such as a stamped metal strip, housed within the telemetry device. In other examples, the conductor element may be a conductive trace included on a printed circuit board (PCB) of the telemetry device. In still other examples, the conductor element may be a shaped metal wire, may be included on a flexible circuit board, may be embedded in ceramic, or may be embedded or applied to the housing of the telemetry device. The variable impedance may be implemented in a variety of different ways. In one example, the variable impedance may include a plurality of different impedances to which the conductor element may be selectively terminated, under control of the telemetry control module. The plurality of impedances may include an open circuit impedance, a conductive termination (e.g., a 50Ω termination), or other passive component termination, such as a capacitor, inductor, or resistor, for example. In other examples, the variable impedance may include adjustable components, the impedance of which may be controlled by the telemetry control module. For example, the variable impedance may include at least one of an inductor, a capacitor, and a resistor which may have controllable inductance, capacitance, and resistance, respectively.

The impedance value of the parasitic element may refer to the total impedance of the combination of the conductor element and the variable impedance. The telemetry control module of the telemetry device may adjust the impedance value of the parasitic element by adjusting the variable impedance that is connected to the conductor element. In examples where the variable impedance is variable to provide a plurality of different impedance values, the telemetry control module may connect the conductor element to a first one of the impedances (e.g., an open circuit) to set a first impedance value of the parasitic element, and may connect the conductor element to a different one of the impedances (e.g., 50Ω termination) to set the impedance value of the parasitic element to a second impedance value that is different from the first impedance value. The first impedance value may produce a first radiation pattern that is different than the radiation pattern produced when the parasitic element is at the second impedance value. In this manner, the telemetry control module may control the radiation pattern of the RF telemetry antenna (i.e., the radiation pattern of the telemetry device) by controlling the impedance value of the parasitic element. In some examples, the parasitic element may have more than two different impedances to which the conductor element may be connected, and the telemetry control module may selectively connect the conductor element to the various impedances in order to select from more than two different radiation patterns.

In examples where the variable impedance includes adjustable components (e.g., resistors, capacitors, and/or inductors), the telemetry control module may adjust the impedance of the adjustable components in order to adjust the impedance value of the parasitic element. Accordingly, in examples where the variable impedance includes adjustable components, the telemetry module may adjust the impedance of the adjustable components to select from a variety of different radiation patterns.

The telemetry control module may adjust the impedance value of the parasitic element in response to the detection of communication errors that occur during communication between the telemetry device and a medical device with which the telemetry device is communicating. The telemetry control module may adjust the impedance value of the parasitic element in response to the detection of communication errors since the detection of errors during communication may indicate that communication between the telemetry device and the medical device is not reliable using the current radiation pattern. The adjustment of the impedance value of the parasitic element may change the radiation pattern, and may therefore lead to a more reliable communication link between the telemetry device and the medical device. In general, the telemetry control module may maintain a current impedance value when errors are not detected during communication between the telemetry device and the medical device since the absence of errors during communication may indicate that the communication between the medical device and the telemetry device is accurate and reliable.

In one example, the telemetry control module may detect errors in data received from the medical device. In other examples, the telemetry control module may determine that data which was previously transmitted from the telemetry device to the medical device was not correctly received at the medical device. The telemetry control module may detect the above errors based on error detection data and acknowledgement data that may be included in the data transferred between the telemetry device and the medical device. The detection of errors during communication between the telemetry device and the medical device are described hereinafter in further detail.

The data transferred between the telemetry device and the medical device may be described herein as packets of data. Each packet of data that is transferred between the telemetry device and the medical device may include a variety of different bit fields. As described herein, the bit fields may include at least one of a payload data field, an error detection field, and an acknowledgement field. The payload data may include information that is retrieved from the medical device, or data that is to be programmed into the medical device. For example, the telemetry device may transmit a packet of data to the medical device that includes payload data that provides programming instructions to the medical device. As an additional example, the medical device may transmit a packet of data to the telemetry device that includes payload data that provides physiological measurements of the patient, such as heart rate, cardiac electrogram data, patient activity data, etc.

Packets of data transferred between the telemetry device and the medical device may include error detection fields (i.e., error detection data). The telemetry device and the medical device may use such error detection fields to determine whether received packets include errors in the payload data or other portions of the packet. Error detection data may include any data that may generally enable a receiving device (e.g., the telemetry device or the medical device) to detect errors in received data (e.g., Reed-Solomon code). Errors may occur as a result of poor RF channel propagation, external or internal generated noise and/or interference, antenna loss, etc. Generally, the detection of errors in data transferred between the telemetry device and the medical device may indicate that the current radiation pattern associated with the RF telemetry antenna may be somewhat unreliable for communication between the telemetry device and the medical device.

With respect to error detection at the telemetry device, the telemetry control module may determine whether the packet received from the medical device includes errors based on error detection data included in the packet received from the medical device. For example, the telemetry device may implement an error detection algorithm using the error detection data to determine whether the payload data of the received packet includes errors. Similarly, with respect to error detection at the medical device, the medical device may determine whether a packet received from the telemetry device includes errors based on an error detection field included in the packet received from the telemetry device. For example, the medical device may implement an error detection algorithm using the error detection data to determine whether the payload data of the received packet includes errors. In examples where the telemetry control module detects an error in the packet received from the medical device, the telemetry control module may adjust the impedance value of the parasitic element in an attempt to prevent future errors.

Packets of data transferred between the telemetry device and the medical device may include acknowledgement data that may indicate whether a previously received transmission was accurately received, or whether the previously received transmission was received with errors. With respect to the medical device, the medical device may generate acknowledgement data that indicates whether a previously received packet included errors, e.g., arising during transmission of data from the telemetry device to the medical device. For example, if the medical device determines that a packet received from the telemetry device included errors, the medical device may transmit acknowledgement data to the telemetry device that indicates that an error was detected in the packet that was previously transmitted by the telemetry device. Alternatively, if the medical device determines that a packet received from the telemetry device did not include errors, the medical device may transmit acknowledgement data to the telemetry device that indicates that no errors were detected in the packet that was previously transmitted by the telemetry device.

The telemetry device may determine whether an error occurred during a previous transmission to the medical device based on the acknowledgment data received from the medical device. In examples where the acknowledgement data indicates that an error occurred during a previous transmission, the telemetry control module may transition the impedance value of the parasitic element from the present impedance value to a different impedance value. The change in impedance value of the parasitic element may modify the radiation pattern of the RF antenna which may provide for more reliable communication with the medical device during subsequent transmissions. In examples where the acknowledgement data indicates that no errors occurred during previous transmissions from the telemetry device to the medical device, the telemetry control module may maintain the present impedance value of the parasitic element since past transmissions from the telemetry device to the medical device proved to be reliable. Although the telemetry device may determine whether an error occurred during a previous transmission to the medical device based on the acknowledgment data received from the medical device, the telemetry device may also determine that an error occurred during a previous transmission to the medical device when no acknowledgement data is received from the medical device, e.g., within a predetermined period of time.

The telemetry device of the present disclosure may have a handheld mobile form factor. In other words, the components of the telemetry device may be included in a housing that may be held and operated in the users hands, e.g., using a single hand. The components of the telemetry device may be included on a PCB and enclosed in a housing. For example, the housing may enclose the PCB, the RF telemetry antenna, the parasitic element, and the variable impedance. The telemetry device may be fabricated in various different sizes. In some examples, the telemetry device may be the size of a handheld portable device such as a cell phone (e.g., approximately 4"×3"×0.5"), or smaller. In other examples, the telemetry device may have a larger form factor such as a tablet computer sized form factor (e.g., 9"×7"×0.5").

The RF telemetry antenna included in the telemetry device may be a helical antenna in some examples. The RF telemetry antenna may be connected to (e.g., soldered) the PCB of the telemetry device. The PCB may include a ground plane that is associated with the RF antenna. The parasitic element may be a serpentine trace on the PCB in some examples. In other examples, as illustrated and described herein, the parasitic element may be a stamped conductor that is supported by the PCB, or by other supporting structures in the housing.

In some examples, the telemetry device of the present disclosure may include a single driven RF antenna that is connected to a receiving and transmitting circuit, along with a parasitic element that may not be driven by a receiving and transmitting circuit, and may not have a direct electrical connection to the receiving and transmitting circuit. The inclusion of only a single antenna in an example telemetry device may decrease the space requirements within the housing of the telemetry device and may allow the housing of the telemetry device to be miniaturized to a handheld form factor that may be held in a single hand. In other examples, however, multiple active antennas may be used in a telemetry device according to the principles of the present disclosure. When multiple active antennas are used, the volume of the housing may be increased in order to accommodate the multiple antennas.

Figure 2:
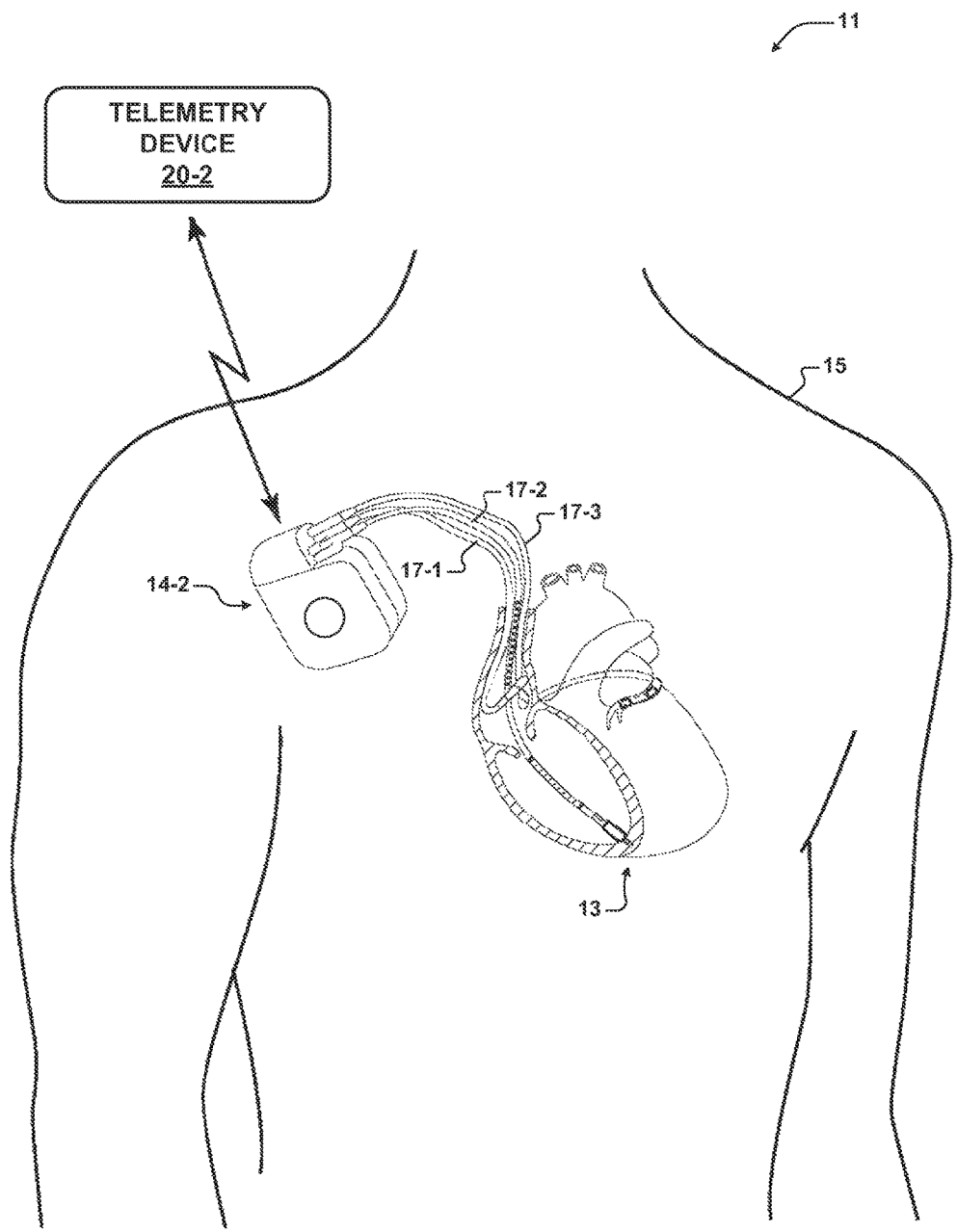
FIG. 2 shows a system that includes an example telemetry device in communication with a cardiac electrical therapy device.

The telemetry device of the present disclosure may be configured to communicate with a variety of different types of medical devices. FIGS. 1-2 show example medical devices with which the telemetry device may communicate. FIG. 1 shows an example implantable medical device (IMD) system that includes an example telemetry device 20-1 of the present disclosure. The example IMD system illustrated in FIG. 1 that communicates with telemetry device 20-1 is a spinal cord stimulation system. FIG. 2 shows another example IMD system that includes an example telemetry device 20-2 of the present disclosure. The example IMD system illustrated in FIG. 2 that communicates with telemetry device 20-2 is a cardiac electrical therapy system. FIGS. 1-2 are meant to show example telemetry devices 20-1, 20-2 that may communicate with example medical devices 14-1, 14-2, respectively. Although example telemetry devices 20-1, 20-2 are illustrated as communicating with a spinal cord stimulation device and a cardiac electrical therapy device, it is contemplated that the telemetry device of the present disclosure may be configured to communicate with other medical devices, both external and implantable, as described herein.

Telemetry devices 20-1, 20-2 of FIGS. 1-2 are merely example implementations of the telemetry device of the present disclosure. In general, with respect to FIGS. 3-6, the telemetry device of the present disclosure may be generally referred to as "telemetry device 20." Additionally, a medical device that may communicate with telemetry device 20 may be generally referred to as "medical device 14." In some examples, telemetry device 20 may implement the functionality of telemetry devices 20-1, 20-2. In other examples, telemetry device 20 may be configured to communicate with medical devices other than those described with respect to FIGS. 1-2. In other words, the telemetry device of the present disclosure may generally be referred to as "telemetry device 20," and the medical device with which telemetry device 20 of the present disclosure may communicate may be referred to as "medical device 14." Telemetry devices 20-1, 20-2 and medical devices 14-1, 14-2 may be viewed as example implementations of telemetry device 20 and medical device 14 described herein. Telemetry device 20 is now described in further detail with respect to FIGS. 1-6.

FIG. 1 is a diagram of an example system 10 for providing electrical stimulation therapy to a patient 12 using an implantable electrical stimulator. In the example of FIG. 1, system 10 includes an implantable electrical stimulator 14-1 (hereinafter "stimulator 14-1") and a telemetry device 20-1. Stimulator 14-1 may be implanted within patient 12. In other examples, stimulator 14-1 may be an external stimulator, e.g., an external neural stimulator, which may be used on a trial basis with percutaneous leads to test stimulation on patient 12. Telemetry device 20-1 may program stimulator 14-1. Telemetry device 20-1 may be implemented as either a clinician programmer or a patient programmer.

As shown in FIG. 1, stimulator 14-1 may be coupled to electrical leads 16A and 16B (collectively "leads 16"). Leads 16 include electrodes (not shown) that deliver the electrical stimulation therapy to patient 12. In some implementations, stimulator 14-1 may include electrodes on the housing of stimulator 14-1 in addition to electrodes on leads 16. In the example of FIG. 1, leads 16 are implanted along the length of spinal cord 18 such that electrical stimulation from leads 16 affects spinal cord 18. In other examples, one or more of leads 16 may be implanted so that electrodes are placed at target locations adjacent deep brain stimulation (DBS) targets, gastric nerves, pelvic nerves, peripheral nerves, and/or a variety of organs such as the heart, stomach, bladder, or the like. Although two leads 16 are shown in FIG. 1, in other implementations, system 10 may include more or less than two leads 16 implanted within patient 12.

Stimulator 14-1 delivers electrical stimulation according to a set of stimulation parameters. Stimulation parameters may include voltage or current pulse amplitudes, pulse widths, pulse rates, electrode combination, and electrode polarity. A combination of the stimulation parameters may be referred to as a "stimulation program." A stimulation program, or multiple stimulation programs, may be stored in stimulator 14-1 and/or telemetry device 20-1. Stimulator 14-1 may provide stimulation according to one or more stimulation programs. For example, stimulator 14-1 may deliver pulses according to the one or more stimulation programs by sequentially delivering pulses from each of the programs, e.g., on a time-interleaved basis.

Using telemetry device 20-1, a user (e.g., a clinician or patient 12) may create one or more customized stimulation programs that define the electrical stimulation delivered to patient 12 by stimulator 14-1. Telemetry device 20-1 may transmit the stimulation programs created by the user to stimulator 14-1. Stimulator 14-1 subsequently generates and delivers electrical stimulation therapy according to the stimulation programs created by the user to treat a variety of patient conditions, as described above. The user may use telemetry device 20-1 to select values for a number of stimulation parameters in order to define the electrical stimulation therapy to be delivered by stimulator 14-1. For example, the user may select stimulation parameters that define a current or voltage amplitude of electrical pulses delivered by the stimulator, a pulse rate, a pulse width, and a configuration of electrodes that deliver the pulses, e.g., in terms of selected electrodes and associated polarities.

Telemetry device 20-1 communicates with stimulator 14-1 via wireless communication. For example, telemetry device 20-1 may communicate with stimulator 14-1 during initial programming of stimulator 14-1, during follow-up programming, or to retrieve data collected by stimulator 14-1. For example, data collected by stimulator 14-1 may include a status of the battery, electrical operational status, lead impedance, and sensed physiological signals. Wireless communication between telemetry device 20-1 and stimulator 14-1 may include RF communication according to standard or proprietary RF telemetry protocols for medical devices in the MICS band.

FIG. 2 shows an example system 11 that may be used to diagnose conditions of and provide therapy to a heart 13 of a patient 15. System 11 includes an IMD 14-2. For example, IMD 14-2 may be an implantable pacemaker, cardioverter, and/or defibrillator that monitors electrical activity of heart 13 and provides electrical stimulation to heart 13.

IMD 14-2 includes leads 17-1, 17-2, 17-3 (collectively "leads 17") that extend into heart 13 of patient 15. IMD 14-2 may sense electrical activity of heart 13 and/or deliver electrical stimulation (e.g., pacing pulses and/or arrhythmia therapy) to heart 13 via electrodes on leads 17 or on the housing of IMD 14-2, e.g., using a unipolar or bipolar combination of electrodes. For example, IMD 14-2 may detect an arrhythmia of heart 13, such as ventricular tachyarrhythmia (VT) or ventricular fibrillation (VF), and deliver antitachycardia pacing (ATP) therapy, cardioversion, or defibrillation therapy to heart 13 in response to the detection of VT/VF. IMD 14-2 may enclose an electrical sensing module that monitors electrical activity of heart 13, and may also enclose a signal generator module that generates therapeutic stimulation, such as cardiac pacing pulses, ATP therapy, cardioversion therapy, and/or defibrillation therapy.

IMD 14-2 and telemetry device 20-2 may wirelessly communicate with one another, e.g., transfer data between one another. Wireless communication between telemetry device 20-2 and IMD 14-2 may include RF communication according to standard or proprietary RF telemetry protocols for medical devices in the MICS band. For example, telemetry device 20-2 may communicate with IMD 14-2 during initial programming of IMD 14-2, during follow-up programming, or to retrieve data collected by IMD 14-2.

IMD 14-2 may send data to telemetry device 20-2, and telemetry device 20-2 may retrieve data stored in IMD 14-2 and/or program IMD 14-2. Data retrieved from IMD 14-2 using telemetry device 20-2 may include cardiac electrograms (EGMs) stored by IMD 14-2 that indicate electrical activity of heart 13 and marker channel data that indicates the occurrence and timing of sensing, diagnosis, and therapy events associated with IMD 14-2. Additionally, data may include information regarding the performance or integrity of IMD 14-2 or other components of diagnostic system 11, such as leads 17. Data transferred to IMD 14-2 using telemetry device 20-2 may include parameters to be programmed into IMD 14-2, for example.

Figure 3:
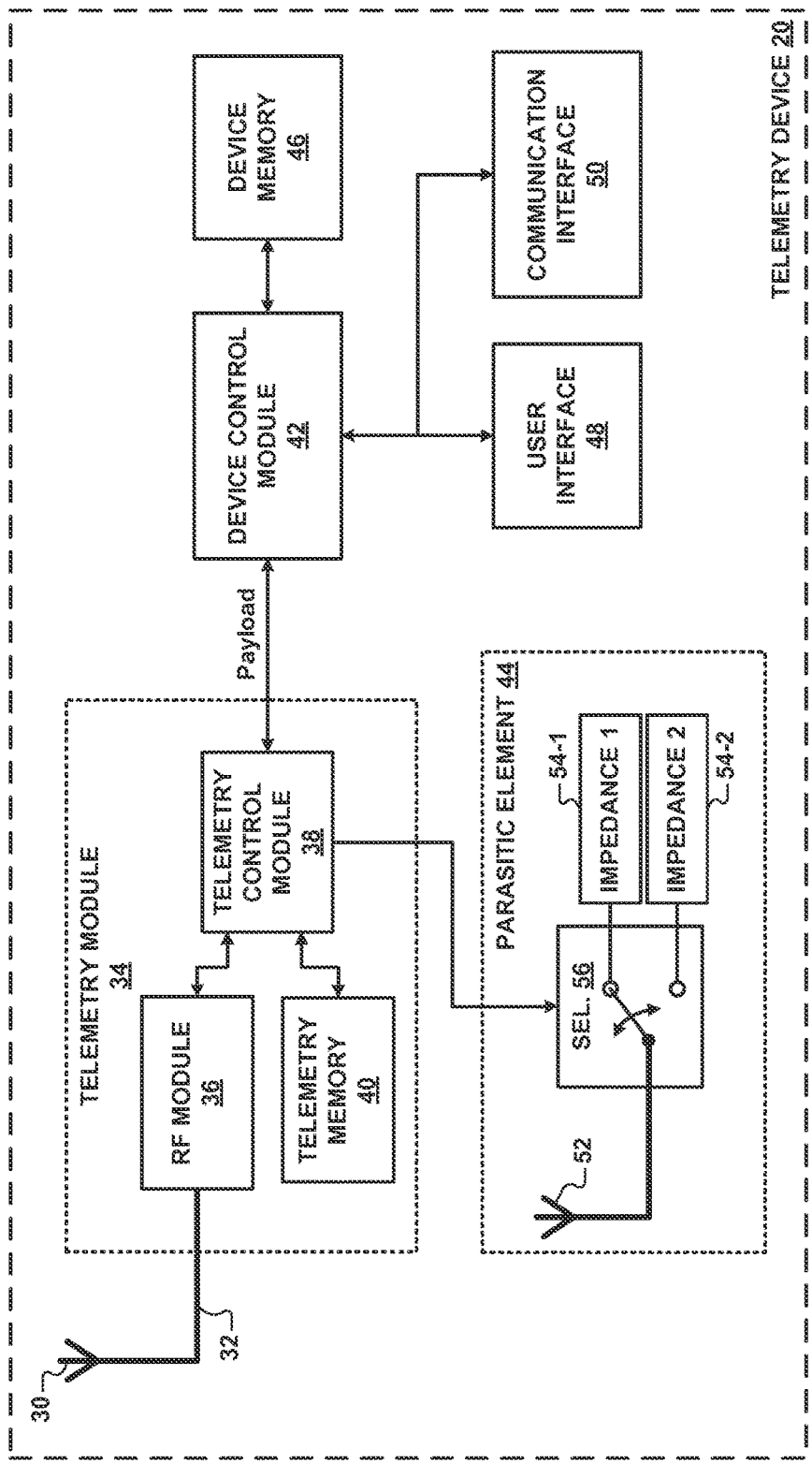
FIG. 3 is a functional block diagram of an example telemetry device.

FIG. 3 shows a functional block diagram of an example telemetry device 20 according to the present disclosure. Telemetry device 20 includes an RF antenna 30, a transmission line 32, and a telemetry module 34 that are configured to transmit data to medical device 14 and receive data from medical device 14. Antenna 30 and transmission line 32 may be configured to send and receive RF signals, e.g., in the MICS band. In some examples, antenna 30 may be a helical antenna that is mounted on a PCB within housing of telemetry device 20.

Modules included in telemetry device 20 represent functionality that may be included in telemetry device 20 of the present disclosure. Modules of the present disclosure may include any discrete and/or integrated electronic circuit components that implement analog and/or digital circuits capable of producing the functions attributed to the modules herein. For example, the modules may include analog circuits, e.g., amplification circuits, filtering circuits, and/or other signal conditioning circuits. The modules may also include digital circuits, e.g., combinational or sequential logic circuits, memory devices, etc. Memory may include any volatile, non-volatile, magnetic, or electrical media, such as a random access memory (RAM), read-only memory (ROM), non-volatile RAM (NVRAM), electrically-erasable programmable ROM (EEPROM), Flash memory, or any other memory device. Furthermore, memory may include instructions that, when executed by one or more processing circuits, cause the modules to perform various functions attributed to the modules herein.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware or software components, or integrated within common or separate hardware or software components.

Telemetry module 34 includes RF module 36, telemetry control module 38, and telemetry memory 40. In general, telemetry module 34 may receive signals from antenna 30 via transmission line 32 and generate digital data that is sent to device control module 42. Additionally, telemetry module 34 may control the impedance value of parasitic element 44. Telemetry memory 40 may include instructions that, when executed by telemetry control module 38, cause telemetry control module 38 to perform various functions attributed to telemetry control module 38 described herein. For example, telemetry memory 40 may include instructions that cause telemetry control module 38 to generate digital data based on signals received from RF module 36, generate data for transmission via antenna 30, detect errors in digital data received via antenna 30, and adjust the impedance value of parasitic element 44.

Figure 4:
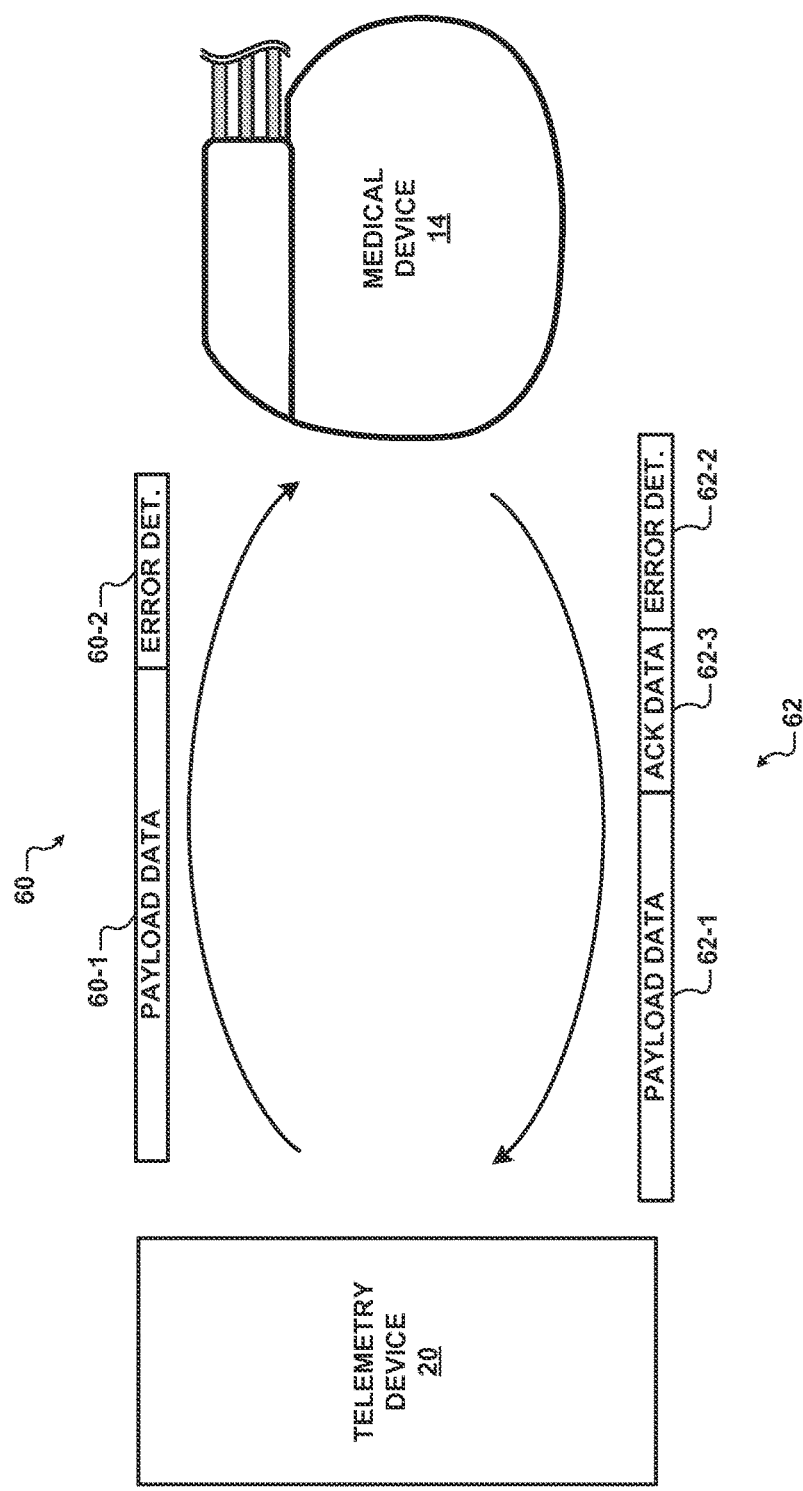
FIG. 4 shows the transfer of packets of data between a telemetry device and a medical device.

RF module 36 may generate digital data based on the signals received from medical device 14 via antenna 30. For example, RF module 36 may receive signals via transmission line 32, demodulate the signals, and perform other signal conditioning operations on the signals to generate digital information (e.g., a packet) included in the signals received from medical device 14. The digital data encoded in the signals received by antenna 30 may be generally referred to herein as a "packet" of data. Accordingly, telemetry control module 38 may receive one or more packets of data that were generated by RF module 36 based on signals received at antenna 30. Telemetry control module 38 may also transfer packets of data to RF module 36 for transmission via antenna 30 to medical device 14. RF module 36 may generate signals for transmission via transmission line 32 and antenna 30 based on packets of data received from telemetry control module 38. Device control module 42 may receive data from telemetry module 34 (i.e., telemetry control module 38) and may also send data to telemetry module 34 (i.e., telemetry control module 38) for transmission via antenna 30. The data transferred between device control module 42 and telemetry module 34 (i.e., telemetry control module 38) may be referred to herein as "payload data," which is illustrated in FIG. 4.

Device control module 42 may control the general functions of telemetry device 20. Device memory 46 may include instructions that, when executed by device control module 42, cause device control module 42 to perform various functions attributed to device control module 42 described herein. Telemetry device 20 may include a user interface 48 with which the user may interact in order to control telemetry device 20. For example, the user may interact with user interface 48 in order to retrieve data from medical device 14 and/or to program medical device 14. User interface 48 may represent a variety of different input and output functionalities included in telemetry device 20. For example, user interface 48 may include a display. Device control module 42 may output information to the display of user interface 48. User interface 48 may also include controls, such as buttons, knobs, a touch screen, etc. Device control module 42 may receive input from the controls of user interface 48. In some examples, user interface 48 may include tactile feedback devices that vibrate in order to indicate an event to the user. Communication interface 50 may include a wired or wireless communication interface that the user may use to transfer data between telemetry device 20 and an external computing device (e.g., a personal computer) (not shown).

Device control module 42 may execute an application stored in device memory 46. The application stored in device memory 46 and executed by device control module 42 may be tailored to the expected use of telemetry device 20. For example, the application may be tailored to operate telemetry device 20 as a cardiac electrical therapy programmer (e.g., a pacemaker, cardioverter, and/or defibrillator). Alternatively, the application may be tailored to operate telemetry device 20 as a neurostimulation device programmer. In still other examples, the application may be tailored to operate telemetry device 20 as a medical device programmer other than a cardiac or neurostimulation device programmer, e.g., as a drug pump programmer.

The application executed by device control module 42 may define how device control module 42 controls the various functions of telemetry device 42. For example, the application may define how device control module 42 displays information on the display of user interface 48 and how device control module 42 responds to inputs from user interface 48. Additionally, the application executed by device control module 42 may define how device control module 42 processes various data, e.g., how device control module 42 sends and receives data via communication interface 50, how device control module 42 generates data to be sent to telemetry control module 38, and how device control module 42 responds to data received from telemetry control module 38.

Telemetry device 20 includes a parasitic element 44 that modifies the radiation pattern of antenna 30. Parasitic element 44 may be included in a housing of telemetry device 20. Parasitic element 44 may generally represent an adjustable impedance value which may be controlled by telemetry control module 38. The radiation pattern (and receive pattern) may depend on the impedance value of parasitic element 44. During operation of telemetry device 20, telemetry control module 38 may selectively adjust the impedance value of parasitic element 44 in order to control the radiation pattern of antenna 30, as described in further detail hereinafter. Parasitic element 44 may modify the radiation pattern and receiving pattern of antenna 30 by reflecting energy that is transmitted from antenna 30 or received from another device. In general, parasitic element 44 may not be electrically connected with a conductor to transmission line 32 or antenna 30.

Parasitic element 44 may include a conductor element 52 (illustrated as an antenna) and a variable impedance (e.g., impedances 54-1, 54-2) that is connected to conductor element 52. In some examples, conductor element 52 may be a conductive object, such as a stamped metal strip, housed within telemetry device 20. In other examples, conductor element 52 may be a conductive trace included on a PCB of telemetry device 20. Impedances 54-1, 54-2 represent impedances to which conductor element 52 may be selectively terminated, under control of telemetry control module 38. Impedances 54-1, 54-2 may represent impedances including, but not limited to, an open circuit impedance, a conductive termination (e.g., a 50 ohm termination), or other passive component termination, such as a capacitor, inductor, or resistor. The selection of the impedance values of impedances 54-1, 54-2 may be based upon the desired radiation patterns of antenna 30. In some examples, impedances 54-1, 54-2 may be passive components (e.g., resistors, capacitors, inductors) that are selectively connected between parasitic element 44 and RF ground.

The impedance value of parasitic element 44 may refer to the impedance value of the combination of conductor element 52 and the impedance to which conductor element 52 is connected (e.g., one of impedances 54-1, 54-2). Telemetry control module 38 may adjust the impedance value of parasitic element 44 by controlling selection module 56 to select one of impedances 54-1, 54-2, thereby adjusting the impedance that is connected to conductor element 52. Selection module 56 may include one or more transistor switches to provide for the switching function associated with selection module 56 herein. Telemetry control module 38 may control selection module 56 to connect conductor element 52 to first impedance 54-1 to set a first impedance value of parasitic element 44, and may connect conductor element 52 to second impedance 54-2 to set the impedance value of parasitic element 44 to a second impedance value that is different from the first impedance value. Antenna 30 may generate a first radiation pattern when parasitic element 44 is at the first impedance value, and antenna 30 may generate a second radiation pattern when parasitic element 44 is at the second impedance value. The first radiation pattern may be different than the second radiation pattern. In this manner, telemetry control module 38 may control the radiation pattern of antenna 30, and telemetry device 20, by controlling the impedance value of parasitic element 44.

Although two different impedances are illustrated and described with respect to FIG. 3, it is contemplated that parasitic element 44 may include more than two impedances in some examples. Additionally, in some examples, telemetry control module 38 may control selection module 56 to connect both first and second impedances 54-1, 54-2 to conductor element 52 at the same time in order to generate a third impedance value, resulting in a third radiation pattern.

Although parasitic element 44 is illustrated and described with respect to FIG. 3 as having discrete impedance values associated with parasitic element 44, it is contemplated that impedances 54-1, 54-2 and selection module 56 may be replaced by a variable impedance element which telemetry control module 38 may control in order to produce varying values of impedance. For example, a variable impedance element may include a passive component having an adjustable impedance value. Such a passive component may include least one of a resistor, a capacitor, and an inductor, which may have values that may be controllable by telemetry control module 38.

Transmission and reception of packets between telemetry device 20 and medical device 14 is now described with reference to FIGS. 3-4. Example packets of data 60, 62 are illustrated in FIG. 4. Packet 60 is an example packet that may include payload data 60-1, generated by device control module 42, and appended error detection data 60-2 generated by telemetry control module 38. Packet 60 may be transmitted via antenna 30 to medical device 14. Packet 62 is an example packet that may include payload data 62-1, error detection data 62-2, and acknowledgement data 62-3. Acknowledgement data 62-3 may have been generated by medical device 14 and appended to packet 62 by medical device 14. Packet 62 is transmitted by medical device 14 to telemetry device 20.

Payload data 62-1 may generally include information that is retrieved from medical device 14. Payload data 60-1 may generally include data to be programmed into medical device 14. With respect to processing of payload data 62-1, RF module 36 may receive signals via transmission line 32 and output packet 62 to telemetry control module 38. Telemetry control module 38 may determine whether packet 62 includes errors. If no errors are detected, telemetry control module 38 may output payload data 62-1 to device control module 42. With respect to payload data 60-1, device control module 42 may generate payload data 60-1 and telemetry module 38 may receive payload data 60-1 from device control module 42, append error detection data 60-2, and output signals to antenna 30 via transmission line 32, thereby transmitting packet 60 to medical device 14.

Payload data 60-1, 62-1 may include any data that is typically transferred between a telemetry device and a medical device. For example, payload data 62-1 may include data measured by medical device 14 for analysis by telemetry device 20, and payload data 60-1 may include program settings to be programmed into medical device 14. The contents of payload data 60-1, 62-1 may also be dependent on the type of system in which medical device 14 and telemetry device 20 are included. In cardiac systems and neurostimulator systems, payload data 60-1 may include parameters to be programmed into medical device 14. In cardiac systems, payload data 62-1 may include cardiac EGMs, marker channel data, and information regarding the performance or integrity of medical device 14. In neurostimulation systems, payload data 62-1 may include a status of the battery, electrical operational status, lead impedance, and sensed physiological signals, for example.

As described above, packets 60, 62 may include error detection data 60-2, 62-2. Upon receiving payload data 60-1 from device control module 42, telemetry control module 38 may generate error detection data 60-2 based on payload data 60-1. For example, telemetry control module 38 may generate error detection data 60-2 using an error detection function that generates error detection data 60-2 based on payload data 60-1. Telemetry control module 38 may append error detection data 60-2 to payload data 60-1 for transmission to medical device 14 as packet 60.

Medical device 14 may determine whether an error occurred during transmission of packet 60 from telemetry device 20 to medical device 14 using error detection data 60-2. For example, medical device 14 may determine whether an error occurred during transmission by using an error detection algorithm that uses error detection data 60-2 to determine whether an error is present in payload data 60-1. Medical device 14 may indicate whether an error occurred during transmission using acknowledgement data 62-3. If medical device 14 determines that an error occurred during transmission of packet 60 from telemetry device 20 to medical device 14, then, during a subsequent transmission from medical device 14 to telemetry device 20, medical device 14 may generate acknowledgment data 62-3 that indicates to telemetry device 20 that an error was detected. If medical device 14 determines that no error occurred during transmission of packet 60, medical device 14 may generate acknowledgement data 62-3 that indicates to telemetry device 20 that an error was not detected during the previous transmission. Telemetry control module 38 may determine whether an error occurred during a previous transmission to medical device 14 based on received acknowledgement data 62-3.

Telemetry control module 38 may adjust the impedance value of parasitic element 44 in response to detection of an error during communication with medical device 14. Telemetry control module 38 may adjust the impedance value of parasitic element 44 by controlling which of impedances 54-1, 54-2 are connected to conductor element 52. For example, telemetry control module 38 may control which of impedances 54-1, 54-2 are connected to conductor element 52 using selection module 56.

In one example, telemetry control module 38 may adjust the impedance value of parasitic element 44 in response to detection of errors in packet 62 received from medical device 14. For example, telemetry control module 38 may determine whether packet 62 received from medical device 14 includes errors based on error detection data 62-2, which medical device 14 may have generated in a similar manner as error detection data 60-2 described above. For example, telemetry control module 38 may implement an error detection algorithm using error detection data 62-2 to determine whether payload data 62-1 includes errors. If packet 62 includes errors, telemetry control module 38 may adjust the impedance value of parasitic element 44 in order to change the radiation pattern (i.e., the receive pattern) of antenna 30. Adjusting the impedance value of parasitic element 44 may adjust the way in which parasitic element 44 reflects energy that reaches it, and may therefore modify the directional strength of the radio waves that are received at antenna 30 and transmitted from antenna 30. Changing the radiation pattern of antenna 30 may help to ensure that subsequently received packets are not received in error. In other words, errors in a received packet may indicate that the radiation pattern of antenna 30 may be inappropriate for receiving data from medical device 14, and the change in the radiation pattern may provide a radiation pattern that may more reliably receive data transmitted from medical device 14 in the future.

As described above, packet 62 transferred to telemetry device 20 may include acknowledgement data 62-3 that indicates whether a packet that was previously transmitted from telemetry device 20 was received at medical device 14 with errors. Telemetry control module 38 receives packet 62 and determines whether acknowledgement data 62-3 indicates that an error occurred during a prior transmission from telemetry device 20 to medical device 14. If acknowledgement data indicates that an error occurred during a prior transmission, telemetry control module 38 may adjust the impedance value of parasitic element 44. For example, telemetry control module 38 may transition the impedance value from a present impedance value to a new impedance value in response to determining that medical device 14 received packets including errors. Since detection of an error that arose during a previous transmission may indicate that the previous transmission was not sufficient to communicate with medical device 14, the radiation pattern change commanded by telemetry control module 38, via the change in impedance, may help to remedy the problems encountered during the previous transmission. In examples where acknowledgement data 62-3 does not indicate that an error was detected during a previous transmission from telemetry device 20, telemetry control module 38 may maintain the impedance value of parasitic element 44 at the current impedance value since the current radiation pattern of antenna 30 is likely sufficient to maintain reliable communications with medical device 14.

Figure 5:
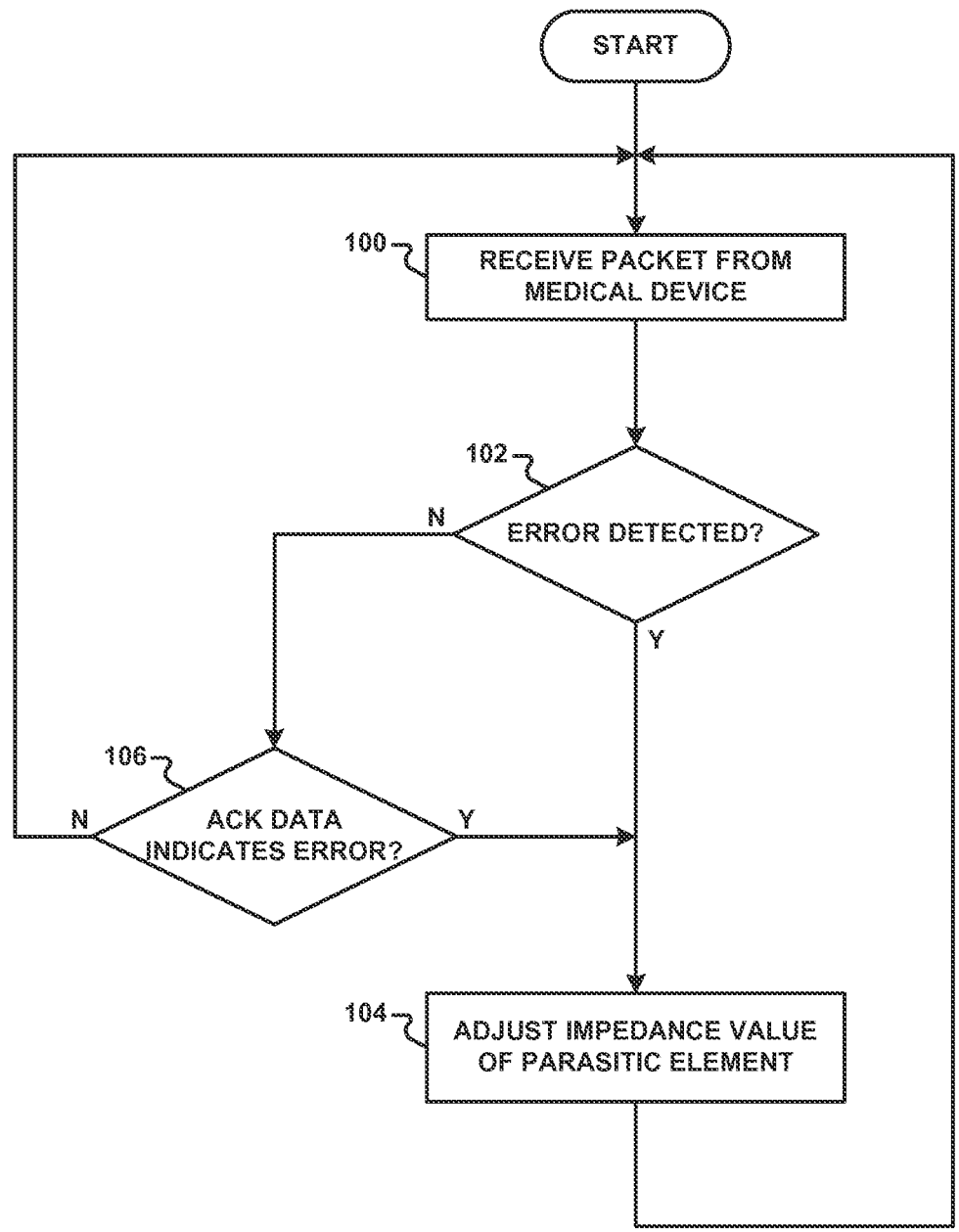
FIG. 5 is a flowchart of an example method for detecting errors in communication between a telemetry device and a medical device, and subsequently adjusting a radiation pattern of the telemetry device in order to prevent future errors.

FIG. 5 is a flowchart of an example method for detecting errors in communication between a telemetry device and a medical device, and subsequently adjusting a radiation pattern of the telemetry device in order to prevent future errors. The method may describe operation of telemetry control module 38 upon receipt of packet 62 from medical device 14. At the start of the method of FIG. 5, it may be assumed that medical device 14 has received one or more packets from telemetry device 20, has generated acknowledgement data 62-3, and has transmitted packet 62 to telemetry device 20.

Telemetry control module 38 may receive packet 62 from medical device 14 via antenna 30, transmission line 32, and RF module 36 (100). Telemetry control module 38 may then determine whether packet 62 includes errors based on error detection data 62-2 (102). If telemetry control module 38 detects errors in packet 62, then telemetry control module 38 may adjust the impedance value of parasitic element 44 (104). If telemetry control module 38 does not detect an error in packet 62 based on error detection data 62-2, then telemetry control module 38 determines whether acknowledgement data 62-3 indicates that a prior transmission from telemetry device 20 to medical device 14 included errors when received by medical device 14 (106). If acknowledgement data 62-3 indicates that an error occurred during a previous transmission, then telemetry control module 38 may adjust the impedance value of parasitic element 44 (104). If acknowledgement data 62-3 indicates that an error did not occur during a previous transmission, then telemetry control module 38 may maintain the current impedance value of parasitic element 44 and continue to block (100). The method of FIG. 5 may be continuously performed by the telemetry device in that telemetry control module 38 may continuously detect errors and adjust the impedance value of parasitic element 44 in response to detection of errors.

Although telemetry control module 38 is described herein as adjusting the impedance value of parasitic element 44 in response to the detection of errors, it is contemplated that telemetry control module 38 may adjust the impedance value of parasitic element 44 in response to other determinations. In one example, telemetry control module 38 may determine a strength of a signal acquired by antenna 30 and adjust the impedance value of parasitic element 44 when the signal acquired by antenna 30 has less than a threshold signal strength. In some examples, a weak signal (e.g., a signal that has less than a threshold strength) may indicate that an adjustment of the impedance value of parasitic element 44 (i.e., the radiation pattern of antenna 30) may provide a stronger signal. In general, telemetry control module 38 may adjust the impedance value of parasitic element 44 in order to reduce error detection by changing the gain, radiation pattern, and/or polarization characteristic of antenna 30.

The errors and signal strength issues that may arise during communication between telemetry device 20 and medical device 14 may arise due to the environment in which telemetry device 20 is located and/or the location of telemetry device 20 relative to medical device 14. Telemetry device 20 could be located in a variety of different environments, such as in a user's hand, in open air, or resting on a table. While one impedance value (e.g., one radiation pattern) may provide reliable communication in one environment, the same impedance value may not provide reliable communication in a different environment. For example, telemetry device 20 may reliably communicate with medical device 14 using a first impedance value while in open air, but may then communicate in an unreliable fashion at the same impedance value when held in a user's hand. In this example, a change in impedance value from the first impedance value to a second impedance value may result in more reliable communication while telemetry device 20 is held in the user's hand.

Figure 6:
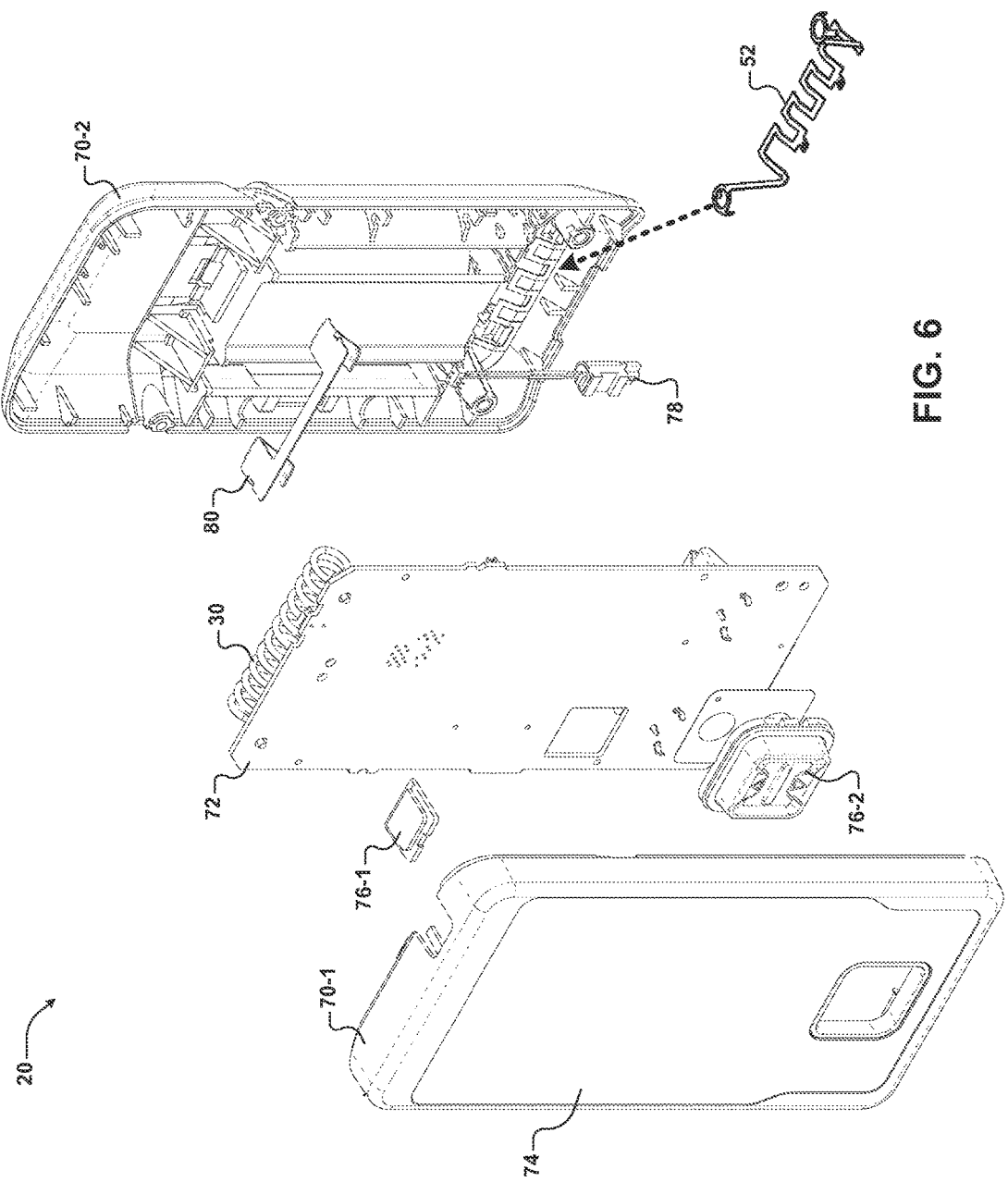
FIG. 6 is an exploded view of an example telemetry device.

FIG. 6 is an exploded view of an example telemetry device 20 according to the present disclosure. Telemetry device 20 may include a housing that encloses components of telemetry device 20. The housing of telemetry device 20 may include a top housing portion 70-1 and a bottom housing portion 70-2. Top housing portion 70-1 and bottom housing portion 70-2 may be fit together such that components of telemetry device 20 are included between top housing portion 70-1 and bottom housing portion 70-2. Top and bottom housing portions 70-1, 70-2, when fit together, may be referred to as "housing 70."

Housing 70 may include a PCB 72 to which some components of telemetry device 20 are mounted. For example, antenna 30 may be mounted to PCB 72. Additionally, components of telemetry module 34 may be mounted to PCB 72, such as telemetry control module 38, RF module 36, and telemetry memory 40. Additionally, device control module 42, device memory 46, and communication interface 50 may be mounted on PCB 72. Although not illustrated in FIG. 6, a ground plane of antenna 30 may also be included on PCB 72. As described above, user interface 48 may include a display, manual controls, such as buttons and a touch screen, and a tactile feedback device. FIG. 6 shows an example display 74 included on top housing portion 70-1 that may allow the user to view data acquired from medical device 14 and/or data to be programmed into medical device 14. Housing 70 also includes buttons 76-1, 76-2 that fit within apertures defined by top housing portion 70-1 and which may be used by the user to interact with telemetry device 20. Tactile feedback device 78 may be included within housing 70. Device control module 42 may control the vibration of tactile feedback device 78 to convey information to the user of telemetry device 20. Telemetry device 20 may also house batteries as a power source for telemetry device 20. Example battery pack tabs 80 for holding batteries in housing 70 are illustrated in FIG. 6.

Housing 70 includes an example conductor element 52. Conductor element 52 mounted in housing 70 is a stamped metal conductive strip in a serpentine shape. Although conductor element 52 is illustrated as a stamped conductive strip in FIG. 6, in some examples, a conductor element may be fabricated on PCB 72 or housed in a dielectric material instead of being included in housing 70 as a stamped conductive strip. Components of parasitic element 44 other than conductor element 52 may be included on PCB 72. Although antenna 30 is illustrated as a helical coil, other antenna geometries are contemplated. For example, antenna 30 could be a folded monopole antenna, an inverted-F antenna on PCB 72, a planar inverted F antenna, etc. A typical distance between antenna 30 and conductor element 52 may be approximately 3 to 8 inches, depending on the operating frequency of antenna 30 and the type of material(s) included in housing 70.

Although the present disclosure describes a telemetry device that may both transmit and receive data via a single RF antenna, the telemetry device of the present disclosure may be modified to include additional communication functionality. For example, the telemetry device may include an additional antenna. In these examples, the telemetry control module may communicate via both the RF antenna and the additional antenna. In some examples, the additional antenna may be an antenna similar to the RF antenna described herein. In other examples, the second antenna may be an inductive antenna configured for inductive telemetry. Such an inductive antenna may generally comprise a wire that is wound to define a core region of the inductive antenna. Additional functionality (e.g., electronic hardware, software, and/or firmware) may be added to the telemetry device to enable the telemetry device to communicate using the inductive antenna when the inductive antenna is included in the telemetry device.

Inductive telemetry and RF telemetry refer to two different wireless communication technologies that may communicate in different frequency bands, include different antenna designs, communicate over a different range of distances, and transmit information at different data rates. Inductive telemetry devices may communicate over a limited distance, e.g., a distance of up to approximately 10 cm. Because of the relatively limited communication distance, inductive telemetry may also be referred to as "proximity telemetry" in some examples. In general, inductive telemetry may rely on modulation of magnetic field signals to transmit and receive telemetry signals.

RF telemetry antennas may be used for communication with medical devices over longer distances than inductive telemetry antennas, e.g., approximately 2-5 meters. Because RF telemetry devices may not require close proximity for communication, RF telemetry may also be referred to as "distance telemetry" in some examples. RF telemetry may operate at approximately 401-406 MHz (e.g., in the MICS band and the MEDS band), or other higher frequency ranges, while inductive telemetry may operate effectively from the Low Frequency (LF) band (e.g., approximately 100 kHz) into medium frequency bands (e.g., approximately 15 MHz), or other lower frequency ranges.

In examples where the additional antenna included in the telemetry device is an inductive antenna, the telemetry device may be configured to communicate with a medical device using either RF telemetry via the RF antenna or inductive telemetry via the inductive antenna. In some examples, the telemetry device may be configured to transmit and receive data via the RF antenna and also transmit and receive data via the inductive antenna. In other examples, the telemetry device may be configured to communicate in one direction using one of the RF and inductive antennas and communicate in the other direction using the other of the RF and inductive antennas. For example, the telemetry device may transmit data to the medical device using the inductive antenna and receive data from the medical device using the RF antenna. Alternatively, the telemetry device may be configured to receive data from the medical device using the inductive antenna and transmit data to the medical device using the RF antenna. Accordingly, inclusion of one or more additional antennas and telemetry schemes (e.g., inductive telemetry) in the telemetry device may allow the telemetry device to communicate with medical devices that are also configured for communication using multiple telemetry schemes (e.g., RF and inductive telemetry).

Although the present disclosure describes a telemetry device that includes an RF antenna and a parasitic element that modifies the radiation pattern of the RF antenna, the techniques of the present disclosure may be applicable to devices other than a telemetry device as described above. For example, the techniques of the present disclosure could be implemented in an implantable or external medical device configured to deliver therapy to a patient or monitor the status of the patient. In such an example, the medical device, such as a pacemaker, cardioverter-defibrillator, or a neurostimulation device may include an RF antenna, a control module, and an adjustable impedance that may be controlled by the control module. During operation of the medical device, the control module may selectively adjust the impedance value of the parasitic element of the medical device in order to control the radiation pattern and receive pattern of the RF antenna of the medical device. For example, the control module may adjust the impedance value of the parasitic element of the medical device in response to the detection of communication errors that occur during communication with a therapy monitoring device such as a patient programmer or patient therapy monitor. The control module of the medical device may adjust the impedance value of the parasitic element of the medical device in response to the detection of communication errors since the detection of errors during communication may indicate that communication between the medical device and the therapy monitoring device is not reliable using the current radiation pattern.

Additionally, in some examples, the medical device may include a second antenna in addition to the RF antenna, as described above. For example, the medical device may include an inductive antenna. In these examples, the medical device may be configured to communicate using the RF antenna and/or the inductive antenna. In some examples, the medical device may be configured to transmit and receive data via the RF antenna and also transmit and receive data via the inductive antenna. In other examples, the medical device may communicate in one direction using one of the RF and inductive antennas and communicate in the other direction using the other of the RF and inductive antennas. For example, the medical device may transmit data to a therapy monitoring device (e.g., a patient programmer or patient therapy monitor) using the inductive antenna and receive data from the therapy monitoring device using the RF antenna. Alternatively, the medical device may receive data from the therapy monitoring device (e.g., a patient programmer or patient therapy monitor) using the inductive antenna and transmit data to the therapy monitoring device using the RF antenna.

Various examples have been described. These and other examples are within the scope of the following claims.

What is claimed is:

1. A device comprising:
   an antenna;
   a parasitic element configured to modify a radiation pattern of the antenna by reflecting energy transmitted from the antenna to increase directional strength of the antenna, wherein the parasitic element has an impedance value that is adjustable, and wherein the radiation pattern of the antenna depends on the impedance value of the parasitic element; and
   a telemetry control module configured to:
      transmit data to a medical device using the antenna;
      receive acknowledgement data from the medical device using the antenna;
      determine, based on the acknowledgement data, that the data transmitted to the medical device included errors upon receipt at the medical device, wherein the acknowledgement data is generated by the medical device based on the data transmitted to the medical device, and wherein the acknowledgement data indicates whether the data transmitted to the medical device included errors upon receipt at the medical device; and
      adjust the impedance value of the parasitic element associated with the antenna in response to the determination based on the acknowledgement data that the data transmitted to the medical device included errors upon receipt at the medical device to improve subsequent data transfer to the medical device.

2. The device of claim 1, further comprising a housing, wherein the housing has a handheld form factor that is configured to be held in a single hand, and wherein the housing encloses the antenna, the parasitic element, and the telemetry control module.

3. The device of claim 1, further comprising a radio-frequency module that is configured to transmit and receive signals having frequencies in a range of approximately 401 MHz to 406 MHz using the antenna.

4. The device of claim 1, wherein the parasitic element comprises:
   a conductor element; and
   a variable impedance that is connected to the conductor element, wherein the impedance value of the parasitic element comprises the impedance of the combination of the conductor element and the variable impedance.

5. The device of claim 4, wherein the telemetry control module is configured to adjust the impedance value of the variable impedance in order to adjust the impedance value of the parasitic element.

6. The device of claim 4, wherein the conductor element comprises at least one of a metal strip and a conductive trace on a printed circuit board.

7. The device of claim 4, wherein the variable impedance comprises a first impedance and a second impedance, wherein the telemetry control module is configured to connect the first impedance to the conductor element to produce a first impedance value of the parasitic element, and wherein the telemetry control module is configured to connect the second impedance to the conductor element to produce a second impedance value of the parasitic element.

8. The device of claim 7, wherein the telemetry control module is configured to adjust the impedance value of the parasitic element from one of the first and second impedance values to the other of the first and second impedance values in response to the determination based on the acknowledgement data that the data transmitted to the medical device included errors upon receipt at the medical device.

9. The device of claim 4, wherein the variable impedance includes at least one of a resistor, a capacitor, and an inductor.

10. The device of claim 1, wherein the telemetry control module is configured to determine a strength of a signal acquired by the antenna, and wherein the telemetry control module is configured to adjust the impedance value of the parasitic element when the determined signal strength is less than a threshold signal strength.

11. The device of claim 1, wherein the parasitic element is configured such that modification of the radiation pattern by the parasitic element comprises modification of a directional strength of at least one of signals transmitted from the antenna or signals received by the antenna.

12. The device of claim 1, wherein the parasitic element is not electrically connected to the antenna.

13. A system comprising:
   a medical device; and
   a telemetry device configured to wirelessly communicate with the medical device, the telemetry device comprising:
      an antenna;
      a parasitic element configured to modify a radiation pattern of the antenna by reflecting energy transmitted from the antenna to increase directional strength of the antenna, wherein the parasitic element has an impedance value that is adjustable, and wherein the radiation pattern of the antenna depends on the impedance value of the parasitic element; and
      a telemetry control module configured to:
         transmit data to the medical device using the antenna;
         receive acknowledgement data from the medical device using the antenna;
         determine, based on the acknowledgement data, that the data transmitted to the medical device included errors upon receipt at the medical device, wherein the acknowledgement data is generated by the medical device based on the data transmitted to the medical device, and wherein the acknowledgement data indicates whether the data transmitted to the medical device included errors upon receipt at the medical device; and adjust the impedance value of the parasitic element associated with the antenna in response to the determination based on the acknowledgement data that the data transmitted to the medical device included errors upon receipt at the medical device to improve subsequent data transfer to the medical device.

14. The system of claim 13, wherein the medical device is an implantable medical device.

15. A method comprising:

modifying a radiation pattern of an antenna by reflecting energy transmitted from the antenna using a parasitic element to increase directional strength of the antenna, wherein the parasitic element has an impedance value that is adjustable, and wherein the radiation pattern of the antenna depends on the impedance value of the parasitic element;

transmitting data to a medical device using the antenna;

receiving acknowledgement data from the medical device using the antenna;

determining, based on the acknowledgement data, that the data transmitted to the medical device included errors upon receipt at the medical device, wherein the acknowledgement data is generated by the medical device based on the data transmitted to the medical device, and wherein the acknowledgement data indicates whether the data transmitted to the medical device included errors upon receipt at the medical device; and adjusting the impedance value of the parasitic element associated with the antenna in response to the determination based on the acknowledgement data that the data transmitted to the medical device included errors upon receipt at the medical device to improve subsequent data transfer to the medical device.

16. The method of claim 15, wherein the parasitic element comprises a conductor element and a variable impedance that is connected to the conductor element, wherein the impedance value of the parasitic element comprises the impedance of the combination of the conductor element and the variable impedance, and wherein adjusting the impedance value of the parasitic element comprises adjusting the impedance value of the variable impedance in order to adjust the impedance value of the parasitic element.

17. The method of claim 16, wherein the variable impedance comprises a first impedance and a second impedance, and wherein adjusting the impedance value of the parasitic element in response to detection of communication errors comprises:

connecting the first impedance to the conductor element to produce a first impedance value of the parasitic element;

connecting the second impedance to the conductor element to produce a second impedance value of the parasitic element; and adjusting the impedance value of the parasitic element from one of the first and second impedance values to the other of the first and second impedance values in response to the determination based on the acknowledgement data that the data transmitted to the medical device included errors upon receipt at the medical device.

18. The method of claim 15, wherein modifying the radiation pattern of the antenna comprises modifying a directional strength of at least one of signals transmitted from the antenna or signals received by the antenna.

19. The method of claim 15, wherein the parasitic element is not electrically connected to the antenna.

20. An apparatus comprising:

means for modifying a radiation pattern of an antenna by reflecting energy transmitted from the antenna using a parasitic element to increase directional strength of the antenna, wherein the parasitic element has an impedance value that is adjustable, and wherein the radiation pattern of the antenna depends on the impedance value of the parasitic element;

means for transmitting data to a medical device using the antenna;

means for receiving acknowledgement data from the medical device using the antenna;

means for determining, based on the acknowledgement data, that the data transmitted to the medical device included errors upon receipt at the medical device, wherein the acknowledgement data is generated by the medical device based on the data transmitted to the medical device, and wherein the acknowledgement data indicates whether the data transmitted to the medical device included errors upon receipt at the medical device; and means for adjusting the impedance value of the parasitic element associated with the antenna in response to the determination based on the acknowledgement data that the data transmitted to the medical device included errors upon receipt at the medical device to improve subsequent data transfer to the medical device.

21. The apparatus of claim 20, wherein the parasitic element comprises a conductor element and a variable impedance that is connected to the conductor element, wherein the impedance value of the parasitic element comprises the impedance of the combination of the conductor element and the variable impedance, and wherein means for adjusting the impedance value of the parasitic element comprises means for adjusting the impedance value of the variable impedance in order to adjust the impedance value of the parasitic element.

22. The apparatus of claim 21, wherein the variable impedance comprises a first impedance and a second impedance, and wherein means for adjusting the impedance value of the parasitic element in response to detection of communication errors comprises:

means for connecting the first impedance to the conductor element to produce a first impedance value of the parasitic element;

means for connecting the second impedance to the conductor element to produce a second impedance value of the parasitic element; and means for adjusting the impedance value of the parasitic element from one of the first and second impedance values to the other of the first and second impedance values in response to the determination based on the acknowledgement data that the data transmitted to the medical device included errors upon receipt at the medical device.

23. A non-transitory computer-readable storage medium comprising instructions that, when executed, cause a programmable processor to:

modify a radiation pattern of an antenna using a parasitic element, wherein the parasitic element has an impedance value that is adjustable and is configured to reflect energy transmitted from the antenna to increase directional strength of the antenna, and wherein the radiation pattern of the antenna depends on the impedance value of the parasitic element;

transmit data to a medical device using the antenna;

receive acknowledgement data from the medical device using the antenna;

determine, based on the acknowledgement data, that the data transmitted to the medical device included errors upon receipt at the medical device, wherein the acknowledgement data is generated by the medical device based on the data transmitted to the medical device, and wherein the acknowledgement data indicates whether the data transmitted to the medical device included errors upon receipt at the medical device; and adjust the impedance value of the parasitic element associated with the antenna in response to the determination based on the acknowledgement data that the data transmitted to the medical device included errors upon receipt at the medical device to improve subsequent data transfer to the medical device.

24. The non-transitory computer-readable storage medium of claim 23, wherein the parasitic element comprises a conductor element and a variable impedance that is connected to the conductor element, wherein the impedance value of the parasitic element comprises the impedance of the combination of the conductor element and the variable impedance, and wherein the computer-readable storage medium further comprises instructions that, when executed, cause the programmable processor to adjust the impedance value of the variable impedance in order to adjust the impedance value of the parasitic element.

25. The non-transitory computer-readable storage medium of claim 24, wherein the variable impedance comprises a first impedance and a second impedance, and wherein the computer-readable storage medium comprises instructions that, when executed, cause the programmable processor to:

connect the first impedance to the conductor element to produce a first impedance value of the parasitic element;

connect the second impedance to the conductor element to produce a second impedance value of the parasitic element; and adjust the impedance value of the parasitic element from one of the first and second impedance values to the other of the first and second impedance values in response to the determination based on the acknowledgement data that the data transmitted to the medical device included errors upon receipt at the medical device.

26. An apparatus comprising:

an antenna;

a parasitic element configured to modify a radiation pattern of the antenna by reflecting energy transmitted from the antenna to increase directional strength of the antenna, wherein the parasitic element has an impedance value that is adjustable, and wherein the radiation pattern of the antenna depends on the impedance value of the parasitic element; and a telemetry control module configured to:

communicate with a wireless device using the antenna;

determine, based on acknowledgement data received during communication with the wireless device, that data previously transmitted to the wireless device included errors upon receipt at the wireless device, wherein the acknowledgement data is generated by the wireless device based on the data previously transmitted to the wireless device, and wherein the acknowledgement data indicates whether the data previously transmitted to the wireless device included errors upon receipt at the wireless device; and adjust the impedance value of the parasitic element associated with the antenna in response to the determination based on the acknowledgement data that the data previously transmitted to the wireless device included errors upon receipt at the wireless device to improve subsequent data transfer to the wireless device.

27. The apparatus of claim 26, wherein the antenna, the parasitic element, and the telemetry control module are configured for implantation in a patient, and wherein the wireless device is a therapy monitoring device.

28. The apparatus of claim 26, wherein the antenna, the parasitic element, and the telemetry control module are included in a therapy monitoring device, and wherein the wireless device is configured to deliver therapy.

29. The apparatus of claim 26, wherein the antenna is a first antenna, and wherein the apparatus further comprises a second antenna.

30. The apparatus of claim 29, wherein the telemetry control module is configured to transmit data using the first antenna and receive data using the second antenna.

31. The apparatus of claim 29, wherein the telemetry control module is configured to receive data using the first antenna and transmit data using the second antenna.

32. The apparatus of claim 29, wherein the first antenna is configured for RF telemetry and the second antenna is configured for inductive telemetry.

* * * * *